(12) United States Patent
Frank

(10) Patent No.: US 12,029,688 B1
(45) Date of Patent: Jul. 9, 2024

(54) HEATED GOGGLE DEVICE

(71) Applicant: David Michael Frank, Aliso Viejo, CA (US)

(72) Inventor: David Michael Frank, Aliso Viejo, CA (US)

( * ) Notice: Subject to any disclaimer, the term of this patent is extended or adjusted under 35 U.S.C. 154(b) by 0 days.

(21) Appl. No.: 18/524,102

(22) Filed: Nov. 30, 2023

Related U.S. Application Data

(60) Provisional application No. 63/524,259, filed on Jun. 30, 2023.

(51) Int. Cl.
*A61F 9/02* (2006.01)
*A61F 7/00* (2006.01)

(52) U.S. Cl.
CPC .............. *A61F 9/029* (2013.01); *A61F 7/007* (2013.01); *A61F 9/026* (2013.01); *A61F 9/027* (2013.01); *A61F 2007/0004* (2013.01); *A61F 2007/0062* (2013.01)

(58) Field of Classification Search
CPC ...... A61F 2007/0004; A61F 2007/0062; A61F 7/007; A61F 2007/0071; A61F 2007/0074; A61F 2007/0093; A61F 2007/0094; A61F 9/02; A61F 9/026; A61F 9/027; A61F 9/029
See application file for complete search history.

(56) References Cited

U.S. PATENT DOCUMENTS

| 11,389,331 | B2 | 7/2022 | Renaud | |
| 2004/0237969 | A1* | 12/2004 | Fuller | A61H 35/02 128/858 |
| 2008/0051741 | A1* | 2/2008 | Grenon | A61F 9/00 607/104 |

(Continued)

FOREIGN PATENT DOCUMENTS

| CN | 206508112 U | 9/2017 |
| CN | 209596179 U | 11/2019 |

(Continued)

OTHER PUBLICATIONS

Blephasteam, Eyelid Warming Mask New Generation, Retrieved From Internet, Retrieved on Nov. 29, 2023, <URL: https://www.blephasteam.com/>.

(Continued)

*Primary Examiner* — Kaitlyn E Smith
*Assistant Examiner* — Bradford C. Blaise

(57) ABSTRACT

The heated goggle device is an easy to use at home dry eye treatment device that uses moist heat to alleviate symptoms caused by MGD and Blepharitis. The goggles include an elastic strap, which is used to affix a pair of heated eyecups over each eye. Electric heaters are attached to the outside of each eyecup, while the inside consists of a raised lattice designed to retain liquid using surface tension. Heat transferred to the inside of the eyecup vaporizes liquid to create a moist warm environment, which is effective in relieving symptoms of dry eye. The user can see through the device during treatment to perform stationary activities such as reading/watching television. Having the eyes open allows the moist heat to directly contact the opening of the oil glands and the action of blinking during a moist heat treatment performs a continuous massaging effect.

16 Claims, 11 Drawing Sheets

(56) References Cited

U.S. PATENT DOCUMENTS

| | | | |
|---|---|---|---|
| 2014/0081361 A1* | 3/2014 | Dhayan | A61F 7/10 |
| | | | 607/109 |
| 2014/0345543 A1* | 11/2014 | Saita | A61F 7/034 |
| | | | 122/21 |
| 2014/0364927 A1* | 12/2014 | Fuller | A61F 9/029 |
| | | | 607/104 |
| 2015/0047649 A1* | 2/2015 | Paulson | A61F 9/026 |
| | | | 128/858 |
| 2016/0302963 A1* | 10/2016 | Yang | A61F 7/007 |
| 2018/0296390 A1 | 10/2018 | Hoare | |
| 2019/0083299 A1* | 3/2019 | Rozanski | A61F 7/02 |
| 2019/0358087 A1* | 11/2019 | Fuller | A61F 9/04 |
| 2021/0121320 A1* | 4/2021 | Sitt | A61F 7/007 |
| 2021/0267793 A1* | 9/2021 | Bruder | A61F 7/03 |

FOREIGN PATENT DOCUMENTS

| | | |
|---|---|---|
| JP | 2014226278 A | 8/2017 |
| WO | 2023127975 A1 | 7/2023 |

OTHER PUBLICATIONS

Dry Eye Mask, Electric Heated Eye Mask, Retrieved From Internet, Retrieved on Nov. 29, 2023, <URL: https://www.dryeyemask.com/>.

Bruder, Finally, Easy-To-Use Pain Relief Solutions!, Retrieved From Internet, Retrieved on Nov. 29, 2023, <URL: https://shop.bruder.com/>.

\* cited by examiner

HEATED GOGGLE DEVICE

FIELD OF THE INVENTION

The present invention generally relates to a heated goggle device. More specifically, the present invention is an easy to use at home dry eye treatment device that uses moist heat to alleviate symptoms of dry eye.

BACKGROUND OF THE INVENTION

In recent years, research has identified MGD (meibomian gland dysfunction) as being one of the leading causes of dry eye type symptoms including dryness, burning, grittiness, scraping, aching, and the feeling of something in the eye. Meibomian glands are oil glands on the inside of the top and bottom of each eyelid and secrete oil (meibum) with each blink to lubricate the ocular surface and prevent tear evaporation. In some people, the glands become inflamed, which can cause oil secretions to turn from an olive oil consistency to that of toothpaste or thicker. This in turn clogs the glands and sets off a cycle of irritation, inflammation and possibly infection, that is difficult to treat due to the eye's sensitive nature. Symptoms arise due to a missing/inefficient protective oil layer, which causes excessive tear evaporation and increased friction between the cornea and inner eyelid. Additionally, any of this meibum that does make it out of the glands, immediately exacerbates symptoms as its thick/gritty composition is spread across the ocular surface. Symptoms of MGD can also be similar to a condition called Blepharitis which includes crusty eyelashes and red/swollen eyelids. Both conditions may exist in tandem and exacerbate symptoms. Patients with these chronic diseases (MGD and Blepharitis) should adhere to a daily regimen of eyelid hygiene to help treat symptoms and keep them at bay. Current treatments involve routinely cleaning the ocular region with mild soaps/cleansers and the application of moist heat to help loosen thickened oils to help unclog the glands and restore their function. Typical applications of moist heat involve warm compresses, which can consist of warm water applied to a washcloth or commercially available microwavable gel bead masks. Both methods suffer by offering little control over the temperature of the compress. Applying the compress at excessive temperature will scald the eyelids (and surrounding areas) and exacerbate symptoms, while not supplying enough heat will render the treatment ineffective. Additionally, due to a narrow clinically effective temperature window, both methods can only shortly maintain an effective temperature, which may also render the treatment ineffective. This shows there is still a need for an at home device that can provide a safe, effective and consistent supply of moist heat in order to obtain the most effective results. Overall, there is still a desire for a home use dry eye treatment device that provides consistent sustained heat, allows the user to see during treatment, and requires no previous component setup or charging for each treatment session. More specifically, there is still a need for an at home device that can provide a safe, effective and consistent supply of moist heat in order to obtain the most effective results.

It is an objective of the present invention to address shortcomings in the current art field with novel enhancements and improvements. In other words, it is the goal of the current invention to provide an at home dry eye treatment device that more easily and effectively reduces symptoms of dry eye. To accomplish this, the present invention comprises an electrically heated pair of eye goggles. More specifically, the present invention is an easy to use at home dry eye treatment device that uses moist heat to alleviate symptoms caused by MGD (Meibomian Gland Dysfunction) and Blepharitis.

Consisting of a swim-like pair of goggles with electric heaters, heat is transferred through the lens to the inside of the eyecup where water is then transformed into therapeutic steam. The device uses this moist heat along with the body's own blinking motion, to remove the buildup of thickened oils caused by MGD, which will help restore oil gland function. Further, the present invention enables users to still use their eyes to do things like watch TV or read during the treatment. In fact, this is crucial to the treatment process as having the eyes open allows the moist heat to directly contact the opening of the oil glands as opposed to having to fully penetrate the closed eyelids. Additionally, the action of blinking during a moist heat treatment performs a continuous massaging effect, whereas any melted/loosened meibum is pumped up and out of the gland openings. During conventional compresses, solidified oils may partially melt just to immediately re-thicken once heat is removed. Thus, the present invention provides a safe, effective and consistent supply of moist heat in order to obtain the most effective results.

SUMMARY

The present invention is a heated goggle device. More specifically, the present invention is an easy to use at home dry eye treatment device that uses moist heat to alleviate symptoms caused by MGD and Blepharitis. Consisting of a swim-like pair of goggles with electric heaters, heat is transferred through the lens to the inside of the eyecup where water is then transformed into therapeutic steam. The goggles include an elastic strap, which is used to affix a pair of heated eyecups over each eye. Electric heaters are attached to the outside of each eyecup, while the inside consists of a raised lattice designed to retain liquid using surface tension. Heat transferred to the inside of the eyecup vaporizes liquid to create a moist warm environment, which is effective in relieving symptoms of dry eye. The user can see through the device during treatment to perform stationary activities such as reading/watching television. This is crucial to the treatment process as having the eyes open allows the moist heat to directly contact the opening of the oil glands as opposed to having to fully penetrate the closed eyelids. Additionally, the action of blinking during a moist heat treatment performs a continuous massaging effect, whereas any melted/loosened meibum is pumped up and out of the gland openings. Thus, the present invention provides a safe, effective and consistent supply of moist heat in order to obtain the most effective results.

DETAIL DESCRIPTIONS OF THE INVENTION

Figure 1:
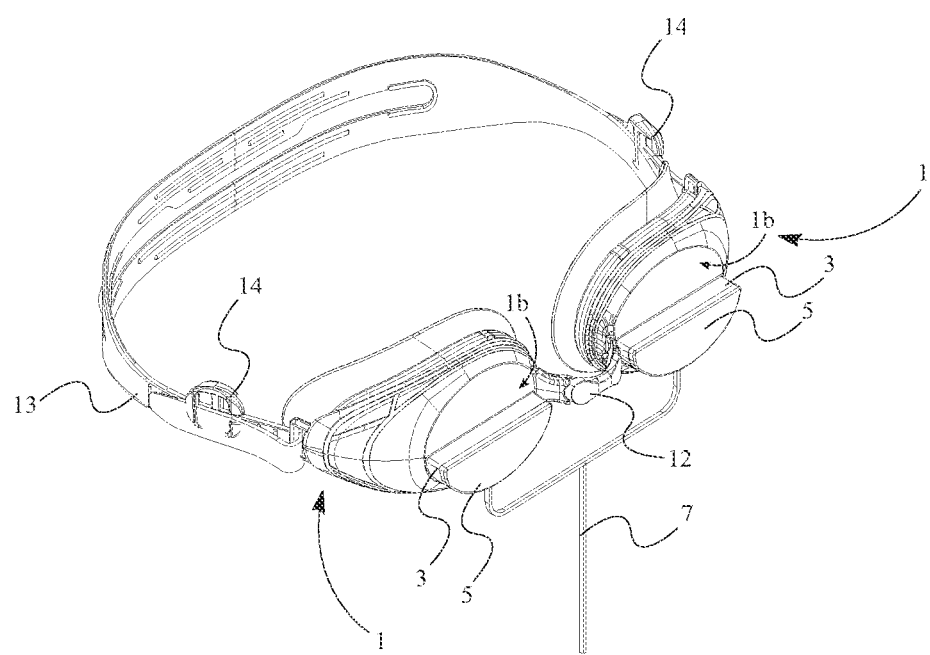
FIG. 1 is a top-front-right perspective view of the present invention, wherein parts of the power cable and the controller device are not shown for clarity.
Figure 2:
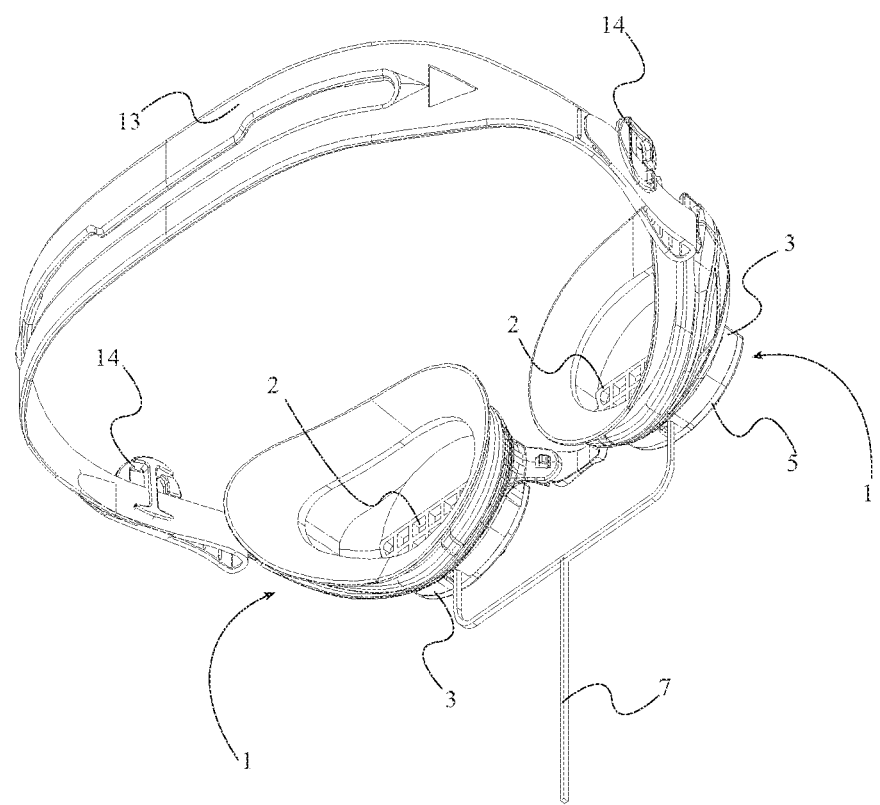
FIG. 2 is a bottom-rear-right perspective view of the present invention.

All illustrations of the drawings are for the purpose of describing selected versions of the present invention and are not intended to limit the scope of the present invention.

In reference to FIG. 1 through FIG. 11, the present invention is a heated goggle device.

The following description is in reference to FIG. 1 through FIG. 11. According to a preferred embodiment, the present invention comprises a plurality of eye cups 1, a plurality of water lattices 2, a plurality of heat receptacles 3, a plurality of heating elements 4, a plurality of covers 5, a controller device 6, a power cable 7, and a power source 8. The plurality of eye cups 1 comprises close-fitting eyeglasses with side shields that covers the entire eyes and eyelids of the user in a snug fashion, and looks similar to swimming goggles. The plurality of eye cups 1 may be shaped in any other way and comprise any other components that are known to one of ordinary skill in the art, as long as the intents of the present invention are not altered.

Figure 3:
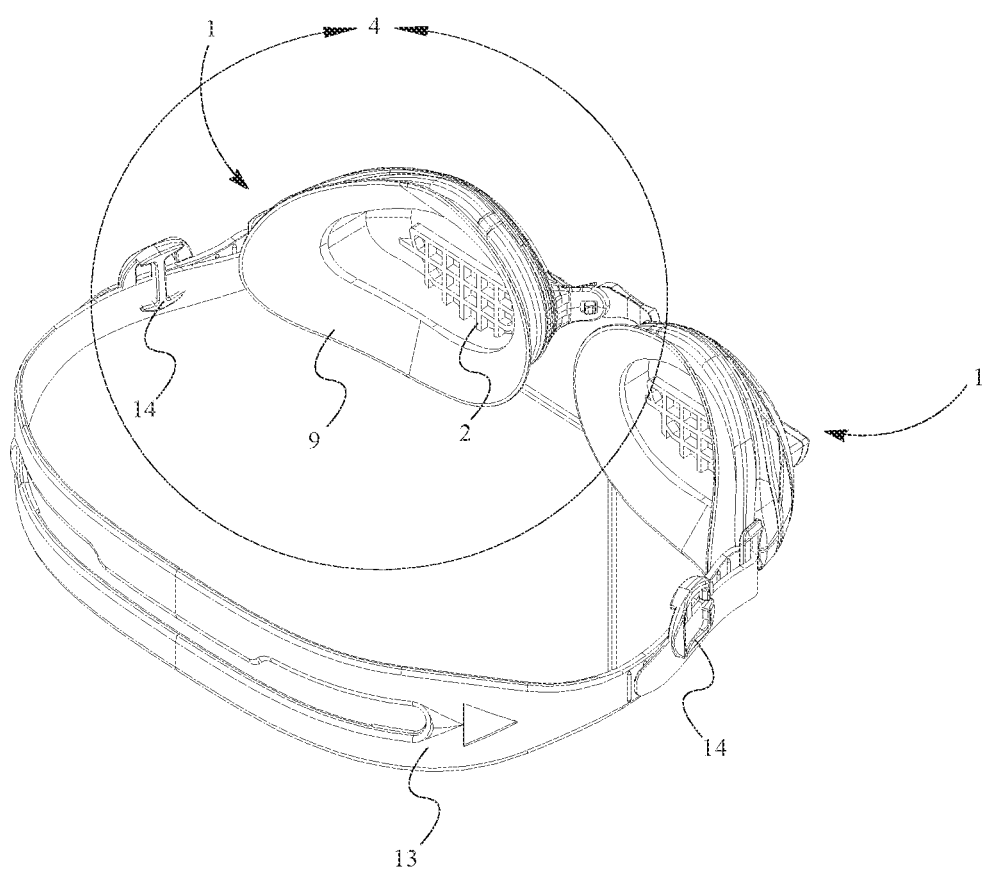
FIG. 3 is a top-rear-right perspective view of the present invention.
Figure 4:
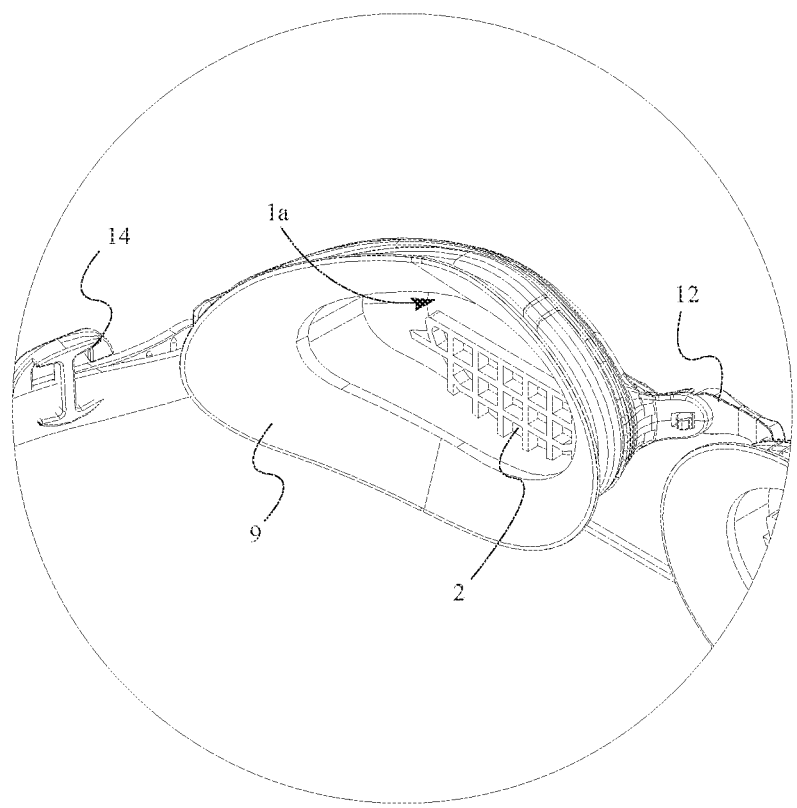
FIG. 4 is a detailed view of section 4 of FIG. 3.

As seen in FIG. 3, and FIG. 4, the plurality of water lattices 2 comprises a raised lattice structure mounted on the inside of the eye cups and is used to retain water. In other words, the plurality of water lattices 2 are lattice-shaped structures made of plastic, whose dimensions and shape enable them to retain water through surface tension. In the preferred embodiment, the plurality of water lattices 2 is mounted onto a first surface 1a of the plurality of eyes cups 1, wherein each of the plurality of water lattices 2 retains water through surface tension. Preferably, the first surface 1a constitutes the inner surface of the eye cups 1 that are facing the user's eyes.

It is an objective of the present invention to provide heat to the water lattices 2 such that hot water vapor or steam is produced within the enclosed eye cups to relieve the dry eye condition of the user. To that end, the plurality of heat receptacles 3 is attached to a second surface 1b of the plurality of eye cups 1, wherein the second surface 1b is positioned opposite to the first surface 1a across the eye cups 1. Preferably, the second surface 1b constitutes an outer surface of the eye cups that is away from the user's eyes. Further, the plurality of heating elements 4 is mounted within the plurality of heat receptacles 3. The plurality of heating elements 4 is mounted on the eye cups 1 in such a way that the plurality of heating elements is in thermal conduction with the plurality of water lattices 2 through the plurality of eye cups 1. In other words, heat is transferred through the material of the eye cup (lens) to the water lattices 2, and water inside the lattice is then transformed into therapeutic steam. This heat also prevents condensation on the first surface 1a of eyecup. Preferably, each of the plurality of heating elements 4 comprises a PTC (positive temperature coefficient) ceramic heater with set temperature of approximately 140 degrees Celsius (+/−5° C.). The PTC ceramic heater is a specific type of heater which uses its specific chemistry to heat up to a specific temperature so that no additional controller is needed. Further, the PTC heater is one of the safest heaters available as it cannot overheat. To provide electrical power to the heating element, each of the plurality of heating elements 4 comprises a solder electrode coating 4a and 4b respectively, to allow soldering of wires to the heating elements 4.

Figure 8:
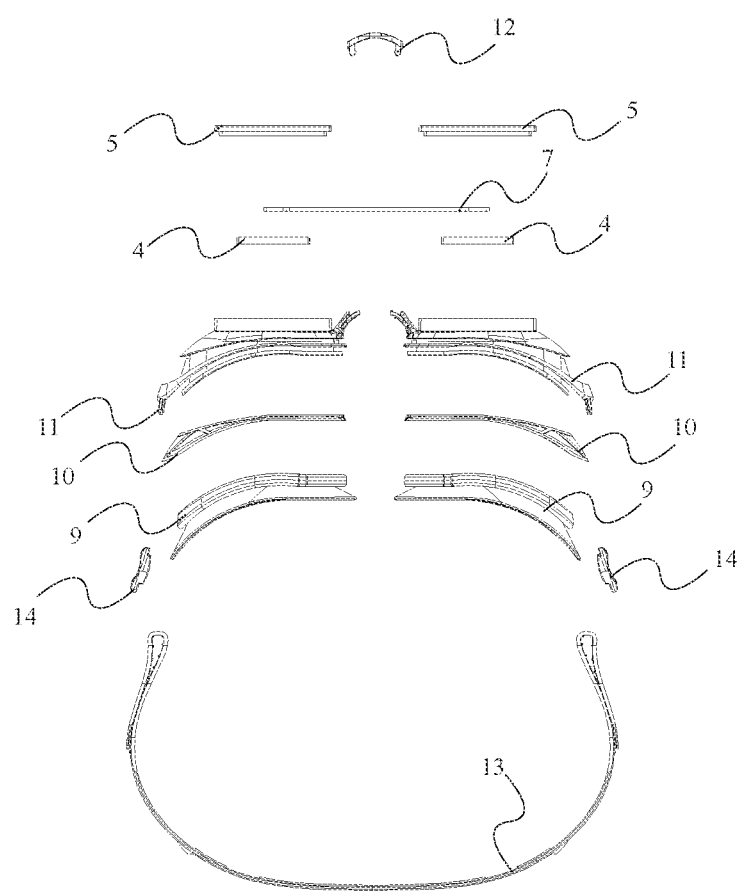
FIG. 8 is an exploded top plane view of the present invention.
Figure 9:
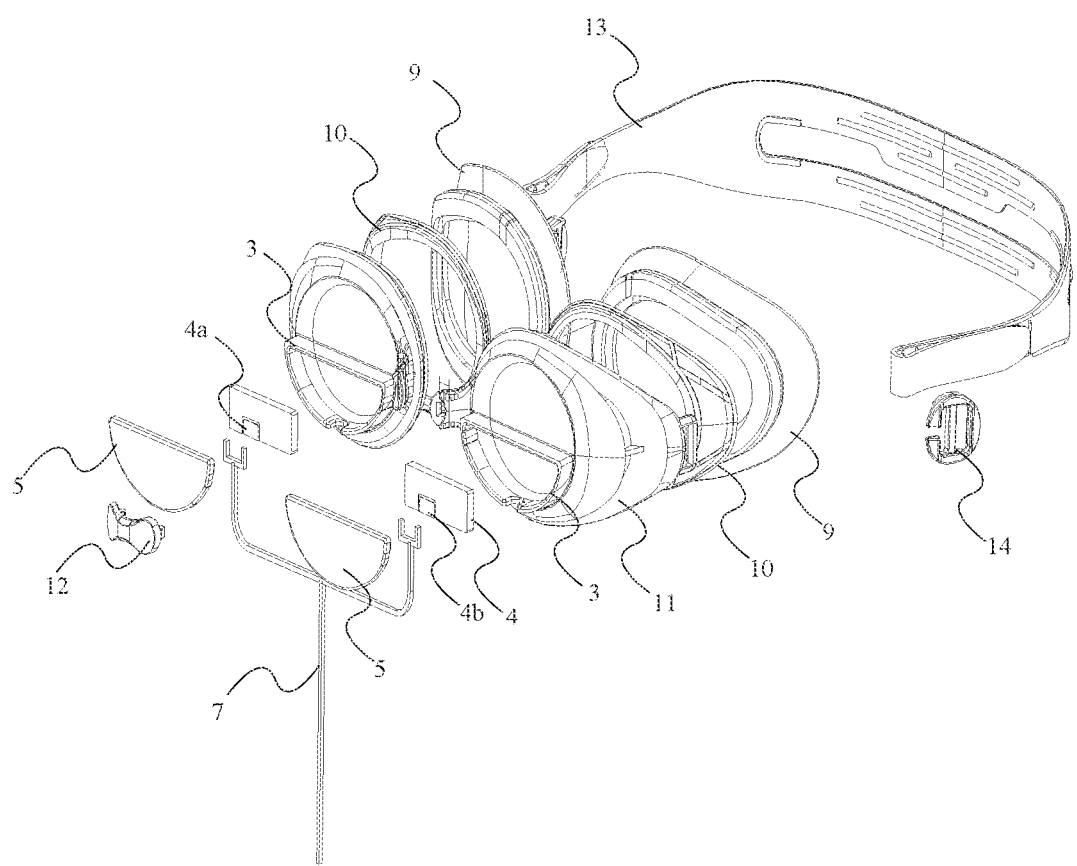
FIG. 9 is an exploded top-front-left perspective view of the present invention.

As seen in FIG. 8 and FIG. 9, the plurality of covers 5 is attached to the plurality of heat receptacles 3, covering the interior of plurality of heat receptacles 3. Preferably, the plurality of covers 5 is made of silicone and has a transverse cross section similar to that of the plurality of heat receptacles 3. In other words, the plurality of covers 5, protects and covers the heating elements 4 mounted within the plurality of heat receptacles 3, as well as protects the users from touching the hot heating element.

According to the preferred embodiment, the plurality of heating elements 4 is affixed to the outside of the eye cups 1 and are connected to the controller device 6 via the power cable 7. More specifically, the controller device 6 is connected between the plurality of heating elements 4 and the power source 8 through the power cable 7. The controller device 6 is the component that can control the operation of the rest of the components of the present invention. To that end, the controller device 6 is electrically and electronically coupled with the plurality of heating elements 4. The power source 8 provides electrical power to the electric and electronic components of the present invention. In the preferred embodiment, the power source 8 is an external wall outlet. However, the power source 8 may comprise any other source such as a rechargeable battery, Lithium-ion battery, solar power, magnetic power, etc., as long as the intents of the present invention are fulfilled.

A more detailed description of the present invention follows.

According to the preferred embodiment, and as seen in FIG. 8 and FIG. 9, each of the plurality of eye cups 1 comprises an eye piece 9, a cosmetic insert 10, and a lens 11. The eye piece 9 is preferably made of silicone and is the piece that will be in contact with the user's face or eye area. The eye piece 9 enables to provide a gentle yet sealed contact of the device around the user's eyes. The cosmetic insert 10 is preferably made of silicone. The cosmetic insert 10 is preferably integrated for aesthetic appeal. In the preferred embodiment, the lens 11 is an injection molded polyether sulfone (PESU) lens that is transparent and enables the user to see through the goggle device. However, it should be noted that the plurality of eye cups 1 may comprise any other materials, size, shape, components, arrangement of components, etc. that are known to one of ordinary skill in the art, as long as the intents of the present invention are not altered. In the preferred embodiment, the plurality of heating elements 4 and the plurality of water lattices 2 are mounted on opposing surfaces of the lens 11.

Figure 5:
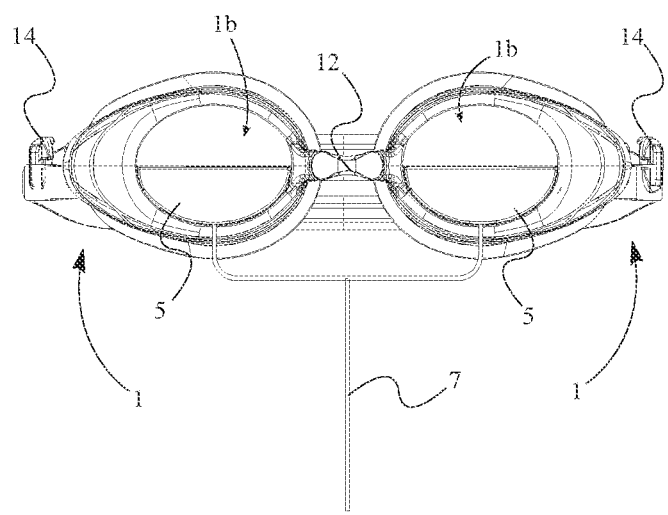
FIG. 5 is a front elevational view of the present invention.
Figure 6:
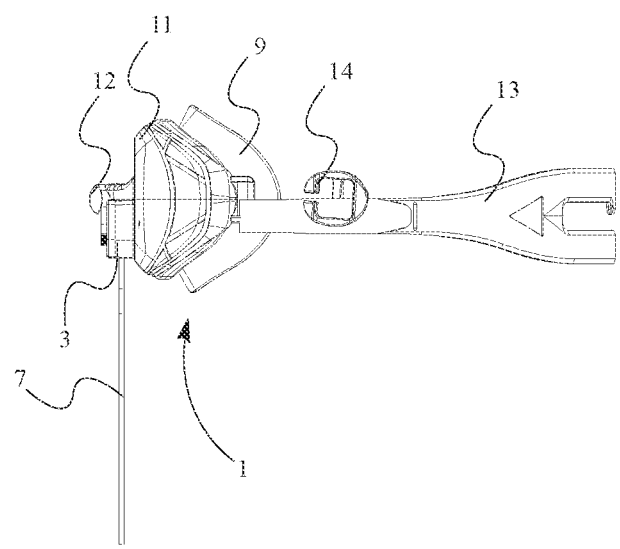
FIG. 6 is left-side elevational view of the present invention.

In reference to FIG. 4, the plurality of water lattices 2 partially covers the first surface 1a of the plurality of eye cups 1, wherein vision through the plurality of eye cups 1 is not obstructed by the plurality of water lattices 2. Similarly, as seen in FIG. 5, the plurality of heat receptacles 3 partially covers the second surface 1b of the plurality of eye cups 1, wherein vision through the plurality of eye cups 1 is not obstructed by the plurality of heat receptacles 3. To that end, in the preferred embodiment, each of the plurality of heat receptacles 3 is semicircular in shape. Further, the plurality of water lattices 2 also comprises a semicircular transverse cross section, such that upper half of the lens 11 is left free for unobstructed vision of the user. This feature of the present invention differs from other warm compresses in that the user can still use their eyes to do things like watch TV or read during the treatment. In fact, this is crucial to the treatment process as having the eyes open allows the moist heat to directly contact the opening of the glands on the lid margin as opposed to having to fully penetrate the closed eyelids.

Figure 7:
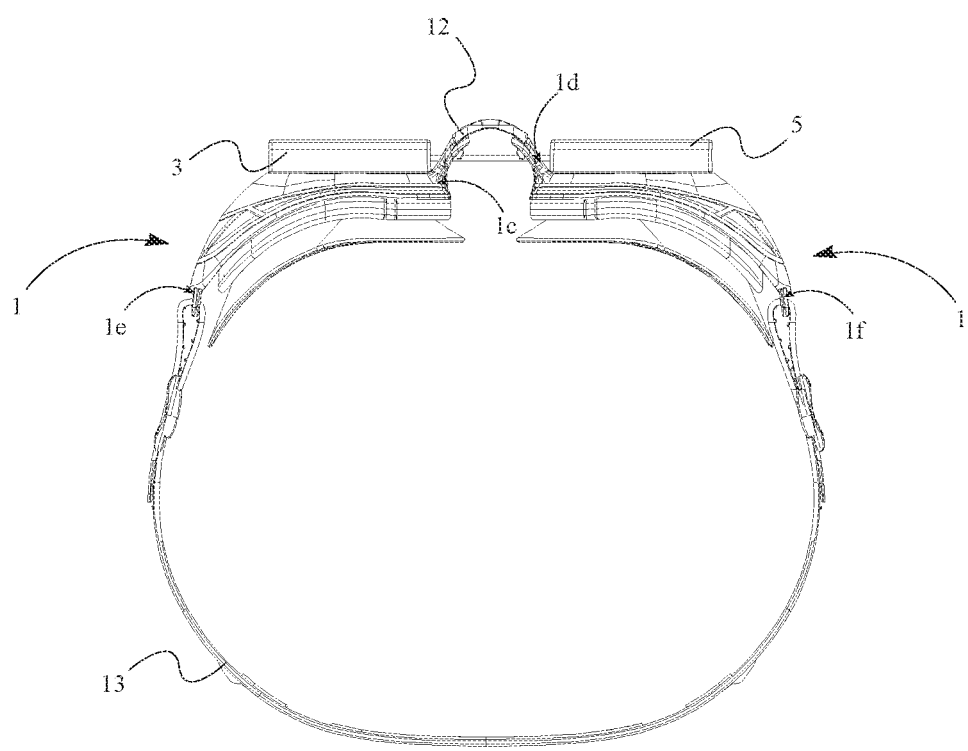
FIG. 7 is a top plane view of the present invention.

As seen in FIG. 1 and FIG. 7, the present invention comprises a nose piece 12 and a head strap 13. Preferably, the nose piece 12 rests on the nose of the user and the head strap 13 enables the user to fasten the present invention around the user's head in a snug fashion. To that end, the nose piece 12 is connected between proximal terminal edges 1c, and 1c of the plurality of eye cups 1, and the head strap 13 is connected between distal terminal edges 1e, 1f, of the plurality of eye cups 1. In other words, the nose piece 12 connects the eye cups from one end, and the head strap 13 connects the eye cups from the opposite end. Preferably, the head strap 13 is made of an elastic material such that the head strap 13 would fit comfortably around the head of the user. Further, in order to provide more adjustment and fit around the people of various head dimensions, the present invention comprises a plurality of adjustment clips 14. Accordingly, the adjustment clips 14 are operably integrated along the head strap 13, wherein operating the adjustment clips 14 enables length adjustment of the head strap 13. Preferably, the adjustments clips 14 are plastic strap adjusters. However, the adjustment clips 14 may comprise any other shape, size, technology, etc. that are known to one of ordinary skill in the art, as long as the intents of the present invention are not altered.

Figure 10:
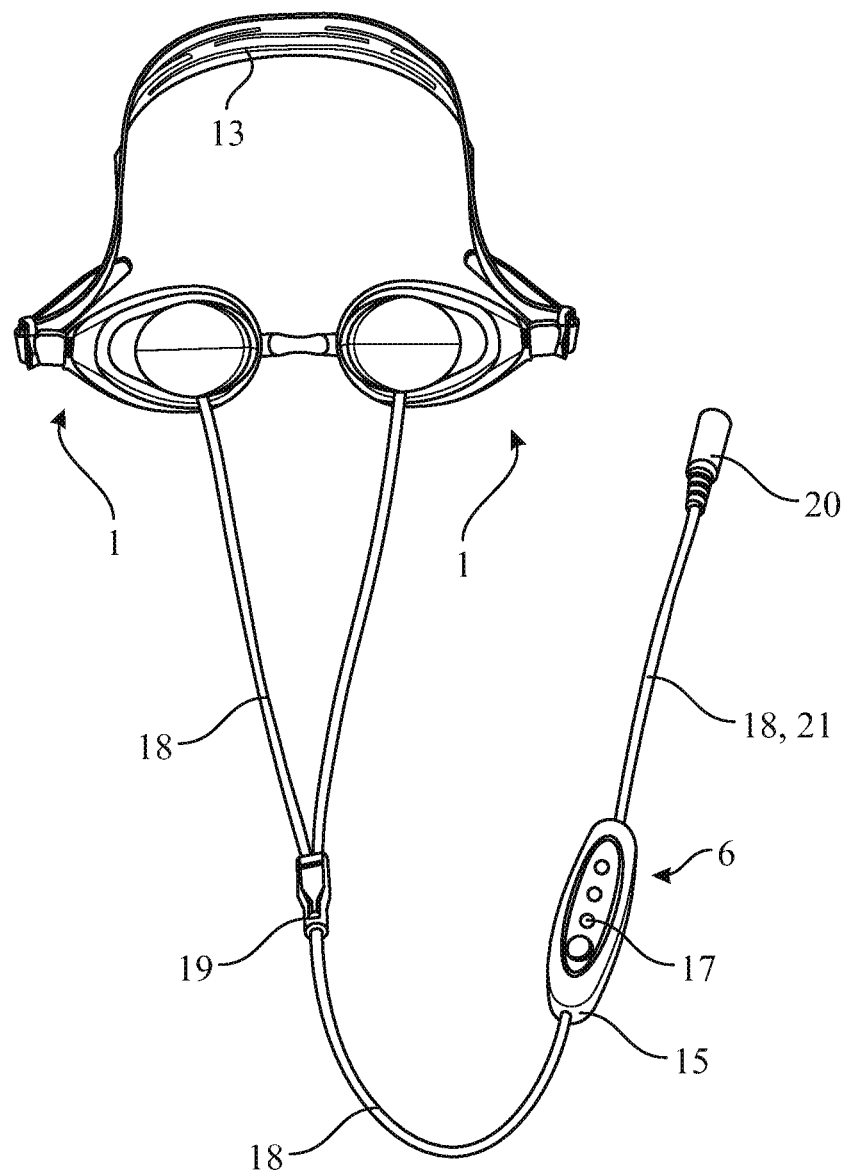
FIG. 10 is a front perspective view of the entire invention.
Figure 11:
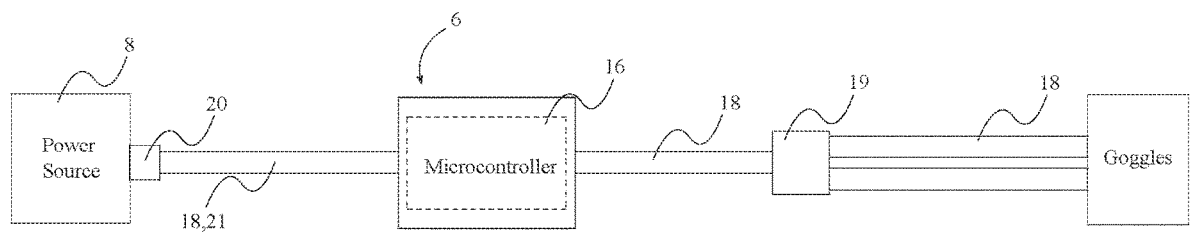
FIG. 11 is a schematic view of the present invention.

As seen in FIG. 10 and FIG. 11, the controller device comprises a controller body 15, a microcontroller 16, and a human interface device (HID) 17. The controller body 15 is a receptacle that houses the microcontroller 16 and the other sensitive components of the present invention in a safe manner. Accordingly, the microcontroller 16 is mounted within the controller body 15, and the power cable 7 is threaded through the controller body 15. Preferably, the microcontroller 16 is a programmable integrated circuit (PIC) that controls the operations of the other components of the present invention. In other words, the microcontroller 16 sends signals from the HID 17 to the heating elements 4 according to the user's preferences. To accomplish this, the microcontroller 16 is electrically connected to the power source 8 through the power cable 7, and the HID 17 is electronically connected to the microcontroller 16. As seen in FIG. 10, the HID 17 is laterally integrated along the controller body 15, and the HID 17 comprises a plurality of timer controls and a power button. Thus, the user may set the timer for a predefined amount of time, such as 10 minutes, 20 minutes, 30 minutes, etc. and have the treatment performed for the selected amount of time. However, the HID 17 may comprise any other size, shape, technology, etc. that are known to one of ordinary skill in the art, as long as the objectives of the present invention are fulfilled. Examples of other HID 17 include, but are not limited to, switches, touch sensitive controls, voice activated controls etc.

Continuing with the preferred embodiment, the power cable 7 comprises a plurality of wire segments 18, a wire splitter 19, and a connection plug 20. As seen in FIG. 10, and FIG. 11, the wire splitter 19 is integrated between the plurality of wire segments 18, and the connection plug 20 is connected to a terminal end of an end segment 21, wherein the end segment is from the plurality of wire segments 18. In the preferred embodiment, the power source 8 is an external wall outlet, to which the connection plug 20 may be connected to, to receive electrical power. However, the power source 8 may comprise any other source and accordingly, the connection plug 20 may also vary. For example, if the power source 8 is a rechargeable battery, then the connection plug 20 may be a USB (universal serial bus) plug.

A preferred method of using the present invention comprises the following steps. To use the device, the user simply sprays water into each eyecup to partially fill each plastic lattice with water. Next, the user will plug the device into a wall outlet, select the desired heating time and place the goggles over their eyes to begin treatment. When the selected time is up, the device powers down and goggles can be removed. The user is recommended to clean their eyes and device with a mild cleanser and rinse with water to remove any oils/debris that have been removed during treatment.

Although the invention has been explained in relation to its preferred embodiment, it is to be understood that many other possible modifications and variations can be made without departing from the spirit and scope of the invention as hereinafter claimed.

What is claimed is:

1. A heated goggle device, comprising:
a plurality of eye cups;
a plurality of water lattices;
a plurality of heat receptacles;
a plurality of heating elements;
a plurality of covers;
a controller device;
a power cable;
a power source;
each of the water lattices mounted onto a first surface of a respective eye cup, wherein each of the plurality of water lattices retains water through surface tension;
each of the heat receptacles attached to a corresponding second surface of the respective eye cup, wherein the second surface is positioned opposite to the first surface across each cup;
each of the heating elements mounted within each of the heat receptacles;
each of the heating elements in thermal conduction with each of the water lattices through each eye cup;
each of the covers attached to a respective heat receptacle, covering each of the heat receptacles;
the controller device connected between the plurality of heating elements and the power source through the power cable; and
the controller device electrically and electronically coupled with the plurality of heating elements.

2. The heated goggle device of claim 1, each of the plurality of eye cups further comprising:
an eye piece;
a cosmetic insert;
a lens; and
the cosmetic insert mounted between the eye piece and the lens.

3. The heated goggle device of claim 2, wherein the lens is transparent.

4. The heated goggle device of claim 1, further comprising:
each of the plurality of water lattices partially covering the first surface of the respective eye cup, wherein vision through each of the eye cups is not obstructed by the respective water lattices.

5. The heated goggle device of claim 1, further comprising:
each of the plurality of heat receptacles partially covering the second surface of the corresponding eye cup, wherein vision through each of the eye cups is not obstructed by the corresponding heat receptacle.

6. The heated goggle device of claim 1, further comprising:
a nose piece;
a head strap;
the nose piece connected between proximal terminal edges of the plurality of eye cups; and
the head strap being-connected between distal terminal edges of the plurality of eye cups.

7. The heated goggle device of claim 6, wherein the head strap is elastic.

8. The heated goggle device of claim 6, further comprising:
a plurality of adjustment clips;
the adjustment clips operably integrated along the head strap, wherein the adjustment clips are configured to enable length adjustment of the head strap.

9. The heated goggle device of claim 1, wherein each of the plurality of heating elements is a positive temperature coefficient (PTC) ceramic heater with a solder coating area.

10. The heated goggle device of claim 1, wherein each of the plurality of heat receptacles is semicircular in shape.

11. The heated goggle device of claim 1, wherein the controller device comprises:
a controller body;
a microcontroller;
a human interface device (HID);
the microcontroller electrically connected to the power source through the power cable;
the microcontroller mounted within the controller body;
the HID laterally integrated along the controller body;
the HID electronically connected to the microcontroller;
the HID electrically connected to the power cable; and
the power cable being-threaded through the controller body.

12. The heated goggle device of claim 11, wherein the HID comprises a plurality of timer controls and a power button.

13. The heated goggle device of claim 1, the power cable comprising:
a plurality of wire segments;
a wire splitter;
a connection plug;
the wire splitter integrated between the plurality of wire segments; and
the connection plug connected to a terminal end of an end segment, wherein the end segment is from the plurality of wire segments.

14. The heated goggle device of claim 1, wherein the power source is an external wall outlet.

15. A heated goggle device, comprising:
a plurality of eye cup;
a plurality of water lattices;
a plurality of heat receptacles;
a plurality of heating elements;
a plurality of covers;
a controller device;
a power cable;
a power source;
a nose piece;
a head strap;
each of the water lattices mounted onto a first surface of of a respective eye cup, wherein each of the plurality of water lattices retains water through surface tension;
each of the heat receptacles attached to a corresponding second surface of the respective eye cup, wherein the second surface is positioned opposite to the first surface across each eye cup;
each of the heating elements mounted within each of the heat receptacles;
each of the heating elements in thermal conduction with each of the water lattices through each eye cup;
each of the covers attached to a respective heat receptacle, covering each of the heat receptacles;
the controller device connected between the plurality of heating elements and the power source through the power cable; and
the controller device electrically and electronically coupled with the plurality of heating elements;
the nose piece connected between proximal terminal edges of the plurality of eye cup; and
the head strap connected between distal terminal edges of the plurality of eye cup.

16. The heated goggle device of claim 1, each of the plurality of eye cup comprising:
an eye piece;
a cosmetic insert;
a lens;
the cosmetic insert mounted between the eye piece and the lens, wherein the lens is transparent; and
each of the heating elements and each of the water lattices mounted on opposing surfaces of the respective lens.

\* \* \* \* \*